| United States Patent [19] | [11] Patent Number: 4,932,995 |
|---|---|
| Escobar | [45] Date of Patent: Jun. 12, 1990 |

[54] PROCESS FOR INCREASING RICE CROP YIELD

[75] Inventor: Jenny Escobar, Guayaquil, Ecuador

[73] Assignee: Rhone-Poulenc Agrochimie, Lyons, France

[21] Appl. No.: 167,008

[22] Filed: Mar. 9, 1988

Related U.S. Application Data

[63] Continuation-in-part of Ser. No. 66,938, Jun. 25, 1987, abandoned.

[51] Int. Cl.$^5$ .............................................. A01N 57/00
[52] U.S. Cl. ......................................................... 71/86
[58] Field of Search ............................................. 71/86

[56] References Cited

U.S. PATENT DOCUMENTS 4,401,454  8/1983  Fritz et al. ................................ 71/76

OTHER PUBLICATIONS

Chaudhuri et al., Indian Agriculturial vol. 24, (1980), pp. 169–175.
Fang et al., Shanghai Agricultural Science and Technology vol. 15(1982) pp. 11–12.
Fang et al., Acun Bonacina Sinica vol. 95 (1983) pp. 344–351.

*Primary Examiner*—Richard L. Raymond
*Assistant Examiner*—Eric J. Kraus
*Attorney, Agent, or Firm*—Morgan & Finnegan

[57] ABSTRACT

Foliar application of a phosphonic acid plant growth regulator to rice crop plants, when the plants are at a growth stage of between about the start of tillering and initiation of panicle primordia, at about 50 to about 750 grams per hectare, results in rice yield significantly greater than untreated rice crops. The invention promotes manipulation of certain physiological processes at vegetative growth stages, thereby reducing decline in tiller number and increasing the number of seed producing tillers.

10 Claims, No Drawings

PROCESS FOR INCREASING RICE CROP YIELD

CROSS-REFERENCES

This application is a continuation-in-part of U.S. Ser. No. 066,938, filed June 25, 1987. now abandoned.

FIELD OF THE INVENTION

The invention relates to a method of increasing rice crop yield which comprises applying to the plant a phosphonic acid plant growth regulator.

BACKGROUND OF THE INVENTION

Compounds having the formula

wherin R, $R^1$ and $R^2$ are as hereinafter defined, are known to induce growth regulating responses in plants, which responses are exemplified but not necessarily limited to ethylene or ethylene-type responses. It is known that ethylene and other gases affect the growth cycle of plants, although the mechanism of this effect is not fully understood. The phosphonic acid compounds generically represented by the formula shown above contain in their structures molecular configurations which are capable of forming ethylene or like compounds.

Plant growth regulators such as phosphonic acid are commonly used to regulate growth of small grain plants such as barley and wheat. Growth of such plants is regulated by applying the plant growth regulator during the growth stage between emergence of flag leaf and boot swelling. This stage is also described as early to late boot stage. Plant growth regulators are not commonly used to regulated growth of rice crops plants.

Fritz et al., U.S. Pat. Nos. 3,879,188, 4,374,661 and 4,401,454, all describe a growth regulation process involving application of certain phosphonic acid compounds having the general formula

where
R is selected from the group consisting of haloethyl and phosphono-ethyl; and
$R_1$ and $R_2$ are selected from the group consisting of
(a) chlorine, hydroxy, and salts thereof;
(b) the group $-OR_3$ and the group $-O-CH_2R_3$ where each R' is one member of the group of unsubstituted aryl, substituted aryl and heterocyclic groups;
(c) the group $-OR_3$ and the group $-O-CH_2R_3$ where each $R_3$ is a different member of the group of hydrogen, unsubstituted alkyl, substituted alkyl, unsubstituted aryl, substituted aryl, heterocycle, alkene and alkyne, provided that when one $R_3$ is selected from the group of unsubstituted alkyl, substituted alkyl, alkene and alkyne, the other $R_3$ is selected from the group of unsubstituted aryl, substituted aryl and heterocycle;
(d) together $R_1$ and $R_2$ represent the group

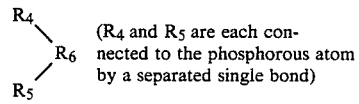

where one of $R_4$ and $R_5$ is $-O-$ and the other is selected from the group of $-O-$, $-OCH_2$, $-CO-O-$ and $CONH$, and $R_6$ represents a cyclic group selected from the group consisting of phenyl, substituted phenyl, heterocyclic ring and substituted heterocyclic ring;
(e) one of $R_1$ and $R_2$ is $-OR_7$ and the other is

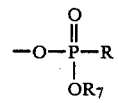

wherein each $R_7$ is the same or different and is selected from the group of hydrogen, unsubstituted alkyl, substituted alkyl, unsubstituted aryl, substituted aryl and a heterocycle group, and wherein R is as previously defined. A preferred phosphonic derivative according to Fritz et al. is 2-chloroethyl phosphonic acid. This preferred derivative is claimed to be useful in hastening ripening in unpicked fruit.

Jacques, U.S. Pat. No. 3,896,163, describes a purification process for separating an aliphatic phosphonic acid such as 2-chloroethyl phosphonic acid from its corresponding half-ester.

Hayakawa et al., U.S. Pat. No. 4,152,429, describe a method for controlling plant fungi and regulating plant growth comprising applying to the plant a composition comprising 2-chloroethyl phosphonic acid and a conventional agricultural fungicide.

Fritz et al., U.S. Pat. No. 4,240,819, describe a method for inhibiting plant growth which comprises applying thereto an effective amount of 2-chloroethyl phosphonic acid.

Fritz et al., U.S. Pat. No. 4,352,689, describe a method for controlling apical dominance which comprises applying to crops an effective amount of 2-chloroethyl phosphonic acid, ranging from about 0.2 lb to about 16 lbs per acre.

Ethephon is the generic name for 2-chloroethyl phosphonic acid marketed under ETHREL ®, PREP ™, CERONE ®, and FLOREL ™ trademarks Ethephon, upon decomposition by a simple base catalyzed reaction, releases ethylene gas. The release of ethylene increases with increasing solution pH. When ethephon is applied to higher plants, ethylene is released in plant cells by the following chemical reaction:

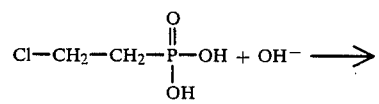

(2-chloroethyl phosphonic acid)

$Cl^- + CH_2=CH_2 + H_3PO_4$.

Ethylene is one of the 5 commonly recognized classes of naturally occurring plant hormones, i.e. Auxins, Gibberellins, Cytokinins, Abscisic acid, and Ethylene. Ethylene is known to play an important regulatory role in various physiological processes, from germination through senescence. Ethephon in liquid form provides a convenient means of ethylene application to plants and is widely used in research for studying ethylene-mediated processes.

Chaudhuri, D., et al., *Indian Agriculturist*, vol 24, pp. 169–175 (1980) describe rice yield increase with foliar application of ethephon or other plant growth regulators at tillering, booting or panicle initiation stages.

Fang, B. C. et al., *Shanghai Agricultural Science and Technology*, vol. 5, pp. 11–12 (1982) and Fang, B. C. et al., *Acta Botanica Sinica*, vol 25, pp. 344–351 (1983) describe rice yield increase with application of ethephon to seedlings of double-cropping second season rice at the 5-leaf stage.

Chaudhuri, D. et al. and Fang et al. do not teach rates of application of ethephon and do not distinguish among the various growth stages of tillering, booting and panicle initiation. The present invention teaches a method for increasing rice crop yield by applying a phosphonic acid plant growth regulator at specific application rates and at a specific plant growth stage.

It is an object of this invention to increase rice grain yield by applying phosphonic acid growth regulators at specific rates and particular stages of plant growth. It is a further object of the present invention to increase the number of seeds and seed producing tillers of a rice crop by applying phosphonic acid growth regulators at rates and plant growth stages which result in manipulation of certain plant physiological processes.

SUMMARY OF THE INVENTION

It has been surprisingly discovered that application of phosphonic acid growth regulators at particular rates and plant growth stages promotes manipulation of certain physiological processes which reduces decline in tiller number and increases the number of seed producing tillers. The presence of high numbers of productive tillers bearing panicles results in high numbers of spikelets per unit land area.

Foliar application of a phosphonic acid plant growth regulator to rice crops at rates from about 50 to about 750 grams per hectare, and preferably from about 100 to about 500 grams per hectare, made between the start of about tillering and initiation of panicle primordia, and preferably between the end of effective tillering and initiation of panicle primordia, promotes sigmificantly greater rice grain yield of said crops.

DETAILED DESCRIPTION OF THE INVENTION

The phosphonic acid compound useful in the present invention is

wherein:
R is selected from the group consisting of haloethyl and phosphonoethyl and
$R^1$ and $R^2$ are selected from
(a) chlorine, hydroxy, and salts thereof;
(b) the group —$OR^3$ and the group —O—$CH_2R^3$ wherein each $R^3$ is a member of the group of unsubstituted aryl, substituted aryl and heterocyclic groups;
(c) the group —$OR^3$ and the group —O—$CH_2R^3$ wherein each $R^3$ is a different member of the group of hydrogen, unsubstituted alkyl, substituted alkyl, unsubstituted aryl, substituted aryl, heterocyclic, alkenyl and alkynyl with the proviso that when one $R^3$ is selected from the group of unsubstituted alkyl, substituted alkyl, alkenyl and alkynyl, the other $R^3$ is selected from the group of unsubstituted aryl, substituted aryl and heterocycle;
(d) together $R^1$ and $R^2$ represent

($R^4$ and $R^5$ are each connected with the phosphorous atom by a separate single bond) where one $R^4$ and $R^5$ is —O— and the other is selected from the group of —O—, $OCH_2$—, —CO—O and CONH, and $R^6$ represents a cyclic group selected from the group consisting of benzene, substituted benzene, heterocyclic rings and substituted hetercyclic rings; or
(e) one of $R^1$ and $R^2$, is —$OR^7$ and the other is:

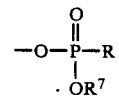

wherein each $R^7$ is the same or different and is selected from the group of hydrogen, unsubstituted alkyl, substituted alkyl, unsubstituted aryl, substituted aryl and a heterocyclic group, and wherein R is as defined hereinbefore.

Reference is hereby made to the following patents and patent applications, the disclosures of which are hereby incorporated by reference: application Ser. No. 617,860, filed Fed. 23, 1967, now abandoned, and applications Ser. No. 617,820, now U.S. Pat. No. 3,531,549 and Ser. No. 617,819 now U.S. Pat. No. 3,551,528, both filed Feb. 23, 1967.

The foregoing applications specified hereinabove disclose preparation techniques for the compounds utilized in the method of the present invention.

Where the term "halo" is used, it is to be understood that this term means the familiar halogens, i.e. fluorine, chlorine, bromine and iodine, so long as an operative growth regulation compound is obtained.

With reference to the general formula utilized in the method of the present invention, preferred groups for substituent R are haloethyl, for example, 2-chloroethyl, 2-bromoethyl and 2-iodoethyl. Preferred half-esters of the phosphonic acid moiety include the 2-chloroethyl mono-ester and the 2-hydroxyphenyl mono-ester. Preferred diesters include the diphenyl and the bis (2-oxo-1-pyrrolidinyl-methyl) esters and as mixed esters, the 2-hydroxyphenyl ester with an alkyl or alkenyl or aryl radical for example, ethyl, isopropyl, propynyl, butyl, octyl, hexadecyl or phenyl radicals. Aryl groups are preferably monocyclic, and bi- or polycyclic aryl groups may be used provided a group to render them soluble (e.g., a sulphonate group), is present thereon.

The term "alkyl" as used herein is intended to include the analogous compounds which have the same growth promotion properties and includes for example cycloalkyl groups, such as cyclohexyl. Preferred alkyl groups are those having up to preferably 18 carbon atoms because above this range, the derivatives are less soluble.

Preferred cyclic esters include those formed with pyrocatechol or mono- or polyhalopyrocatechol derivatives, for example 4-chloropyrocatechol or tetrachloropyrocatechol; with salicyclic acid, with saligenin, and with 2,3-pyridinediol. Another preferred derivative is the acid chloride.

Specific phosphonic acids and derivatives thereof suitable for use in this invention include:
1. 2-choloroethyl phosphonic acid.
2. The bis(acid chloride) or 2-chloroethyl phosphonic acid.
3. The pyrocatechol cyclic ester of 2-chloroethyl phosphonic acid.
4. The 4-chloropyrocatechol cyclic ester of 2-chloroethyl phosphonic acid.
5. The mixed ethyl and 2-hydroxyphenyl diester of 2-chloroethyl phosphonic acid.
6. The mixed butyl and 2-hydroxyphenyl diester of 2-chloroethyl phosphonic acid.
7. The mixed propynyl and 2-hydroxyphenyl diester of 2-chloroethyl phosphonic acid.
8. The 2-chloroethyl monoester of 2-chloroethyl phosphonic acid.
9. 2-bromoethyl phosphonic acid.
10. The bis (phenyl)-ester of 2-chloroethyl phosphonic acid.
11. The tetrachloroprocatechol cyclic ester of 2-chloroethyl phosphonic acid.
12. 2-iodoethyl phosphonic acid.
13. The saligenin cyclic ester of 2-chloroethyl phosphonic acid.
14. Salicyclic acid cyclic ester of 2-chloroethyl phosphonic acid.
15. Phosphonoethyl phosphonic acid.
16. Phosphonoethylthioethyl phosphonic acid.
17. The 3-hydroxyphenyl monoester of 2-chloroethyl phosphonic acid (which exits in polymeric form).
18. The bis(2-oxo-pyrrollidinylmethyl) ester of 2-chloroethyl phosphonic acid.
19. The 2-hydroxyphenyl monoester of 2-chloroethyl phosphonic acid.
20. The mixed isopropyl and 2-hydroxyphenyl diester of 2-chloroethyl phosphonic acid.
21. 2-fluoroethyl phosphonic acid.
22. The mixed octyl and 2-hydroxyphenyl diester of 2-chloroethyl phosphonic acid.
23. The mixed hexadecyl and 2-hydroxyphenyl diester of 2-chloroethyl phosphonic acid.
24. The mixed tridecyl and 2-hydroxyphenyl diester of 2-chloroethyl phosphonic acid.
25. The anhydride of 2-chloroethyl phosphonic acid.
26. The mixed butyl and 2-hydroxphenyl diester of 2-chloroethyl phosphonic acid.
27. The 2-chloroethylester of 2-chloroethyl of phosphonic acid.

2-chloroethyl phosphonic acid is preferred.

The phosphonic acid compounds used in the process of this invention are generally soluble in water. In instances where these compounds are not appreciably water soluble, it has been found that contact with water frequently causes sufficient hydrolysis to result in a soluble product thereby obviating the necessity of utilizing sophisticated formulations containing surfactants, dispersing agents, extenders, etc. However, if desired, the compounds used in the process of this invention may be absorbed onto solid carriers such a vermiculite, attaclay, talc and the like for application via a granular vehicle.

Application may be by any conventional means which provides uniform application of the plant growth regulator, such as a hand-held $CO_2$ charged sprayer system, backpack sprayer system, tractor-drawn sprayer, or other conventional ground or aerial application system when the active compounds are in solution and conventional solid material application systems when the active compounds are absorbed onto solid carriers.

Compositions useful in this invention can be prepared by conventional mixing methods. Suitable liquid diluents or carriers include water, petroleum distillates, or other liquid carriers with or without surface active agents. Due to the good solubility of phosphonic acid compounds in water, water is preferred.

The required amount of the active ingredient contemplated herein may be applied along with inert carrier at a rate per acre of from about 1 to about 200 gallons of liquid carrier and/or diluent or of from about 5 to about 500 pounds of inert solid carrier and/or diluent. Higher rates may also be used. The concentration in the liquid concentrate will usually vary from about 5 to about 95 percent by weight and in the solid formulation from about 0.5 to about 90 percent by weight.

Formulations useful in the present invention can also contain other optional ingredients such as stabilizers or other biologically active compounds. It is preferable that optional ingredients do not harm the plant being treated and do not impair or reduce the activity of the active ingredient. Biologically active compounds include, for example, one or more insecticidal, herbicidal, fungicidal, nematicidal, miticidal, plant growth regulators or other known compounds. Such optional ingredients may be used for their known purpose as well as for any synergistic effect they may provide.

Treatment of rice crops in accordance with the present invention promotes
increase in number of panicles per unit land area;
increase in number of panicles per plant;
increase in grain weight;
increase in number of grains per panicle;
increase in plant height;
increase in straw stiffness; and
reduction in number of sterile florets per panicle.

In accordance with the present invention, the phosphonic acid compound is applied to rice crops at rates from about 50 to about 750 grams per hectare, preferably about 100 to about 500 grams/ha, more preferably from about 200 to about 400 grams/ha, and even more preferably from about 240 to about 360 grams/ha. Application is during the rice crop growth stage between about the start of tillering and initiation of panicle primordia and preferably between the end of effective tillering and initiation of panicle primordia. More preferably application is about 7–10 days before initiation of panicle primordia. Application after initiation of panicle primordia period of time between the end of effective tillering and initiation of panicle primordia occurs between about 45 and about 90 days after seeding.

The end of effective tillering is defined as the period when the tillering number reaches that of eventual panicle number at maturity. It immediately precedes the period when the plant has a maximum number of tillers. This period is often observed when vegetive growth slows markedly and floral development begins, and is defined for a given rice crop variety. Weather conditions do not significantly change the timing of this rice crop growth stage period.

ETHREL® 480 ethephon is one of several suitable sources of ethephon. It has a concentration of ethephon of 480 grams active ingredient per liter solution.

Suitable rice varieties which may be treated according to the present invention include but are not limited to IRRI cultivarus saturn, INIAP 415 [F1(IR930X-IR579)×F2(IR930XIR22)], CR-1113, and Ecuador Juma 57.

EXAMPLES

EXAMPLE 1

Saturn variety rice was planted May 13, 1981 near Rosa, Louisiana. Prior to planting, 20-40-60 units of N-P-K were applied. On June 1, 1981, 4 pounds ai/ac of propanil were applied. On July 9, 1981, 160 units of ammonium nitrate were applied, and on July 24, 1981, ETHREL® ethephon was applied in amounts of either 114 g ai/ac or 227g ai/ac. A control planting having no ETHREL® ethephon treatment was also maintained. The aforementioned treatments were separated by permanent soil levees, and replications or sub-plots were separated on all sides by 3-foot alley ways. Each plot was 6 feet by 30 feet.

The treatment solution was applied using a hand-held $CO_2$ charged 2-gallon sprayer system. This system has a two-row boom equipped with Tee-jet diaphragm check valve nozzles having 8004 HSS flat fan tip and 100 mesh screens.

The number of panicles per unit area was determined by placing a 9 ft$^2$ frame over the rice crop and removing all panicles from plants within this area. Each panicle was cut ¼-½ inch below the last joint. The average weight per panicle was then determined.

The weight of individual seeds was determined by treatment. These 1000 grains were weighed, and the mean weight per seed was calculated.

To make appropriate plant measurements, twenty-five plants were selected at random from each plot on September 21 and used to determine panicle to flag leaf measurements. Two measurements were recorded on each plant. The first was the length from the flag leaf to the base of the panicle, and the second was the length from the flag leaf to the tip of the panicle.

The entire plot, less the area used to determine number of panicles per unit area, was harvested on Oct. 2, 1981 using a small plot combine. The rice seed from each plot was weighted.

Results

The measurements from the tip and base of the panicle to the flag leaf are presented in Table II. Variation in lengths among panicles within the plots was considerable.

Table III presents information on panicle numbers, the weights of each panicle, the weight of 1000 grains and the yield of rice product by each treatment. The plots with 227 g ai/ac of ETHREL® ethephon produced a significantly heavier panicle than the plots with 114 g ai/ac ETHREL® ethephon or the control plots. Also the plots with 227 g ai/ac of ETHREL® ethephon had a higher weight per 1000 grains (25.15 gms) and yielded significantly more rice than the other plots.

TABLE II

| Treatment | (g ai/ac) | Length (cm) of flag leaf to panicle | | |
|---|---|---|---|---|
| | | base of panicle | tip of panicle | overall |
| ETHREL® | 114 | 2.5 | 21.6 | 24.1 |
| ETHREL® | 227 | 2.7 | 21.7 | 24.4 |
| Control | — | 3.1 | 21.0 | 24.1 |

TABLE III

| Treatment | (g ai/ac) | Yield$^a$ (lb/ac) | Weight/ 1000 grains (g) | Number panicles per 9 ft$^2$ | Weight/ panicle (g) |
|---|---|---|---|---|---|
| ETHREL® | 114 | 2498.3 b | 24.12 b | 491.9 | 0.445 c |
| ETHREL® | 227 | 3398.4 a | 25.15 a | 462.4 | 0.656 a |
| Control | — | 2341.3 b | 24.02 b | 452.5 | 0.507 b |

$^a$Means followed by the same letter in the same column do not differ significantly at the 5% level of probability according to Duncan's multiple range test.

No phytotoxicity was observed during these treatments with ETHREL® ethephon.

EXAMPLE 2

INIAP 415 [F1 (IR930×IR579)×F2 (IR930×IR22)] variety rice was planted in April, 1982 in Ecuador. Crops were treated with ETHREL® 480 ethephon in June 1982, at rates of either 500 or 1000 ml/ha. A control planting having no ethephon treatment was also maintained. Plot size for each of the treatments was 500 m$^2$. Soil type used in the experiment was clay, and precipitation was about 170 mm/month. Urea fertilizer (46% ai) was used at 500 lb/ha in three applications. Weed control was maintained by applying a mixture of 5 liters propanil, 3 liters butachlor and 600 ml 2,4-DP, Dichloraprop per hectare ten days after transplanting.

Phytotoxicity was measured by observing chlorosis, necrosis, color change of roots, root deformation, height reduction of plants, reduction of stand, etc. A numerical scale of 1 (no phytotoxicity) to 5 (total kill) was used to represent degree of phytotoxicity. Number of tillers per square meter was measured using a 0.25 m$^2$ frame thrown 4 times at random in the test plot. A similar procedure was used to determine number of panicles/m$^2$ at the time plants were physiologically mature. Plant height at harvest was measured from the ground to the top of the flag leaf. Four random measurements per plot were made. Yield was taken by harvesting the total plot area, and is represented in MT/ha with 14% grain moisture.

Results

Table IV presents data of the experiment.

TABLE IV

| PARAMETER | Control | ETHREL® (g ai/ha) | |
|---|---|---|---|
| | | 240 | 480 |
| Phytotoxicity | — | None | None |
| No. of tillers/m$^2$ | 309 | 309 | 308 |
| No. of panicles/m$^2$ | 246 | 278 | 292 |
| Sterile panicles (%) | 8.4 | 5.6 | 5.0 |
| Plant height (cm) | 104 | 113 | 117 |
| Grain yield (MT) | 5.8 | 8.1 | 8.2 |

Application of ETHREL® ethephon at both concentrations significantly increased panicle number, plant height, and grain yield, and substantially decreased the percentage of sterile panicles.

EXAMPLE 3

Ecuador developed rice variety rice No. 1001, also called Juma 57, was planted in Ecuador during the dry season and harvested during the wet season of 1985. ETHREL® 480 ethephon treatment was done 67 days after planting, at the stage when the flower primordia was just formed (about 5 mm. in length). Application rates were either 120, 240 or 360 g/ha (0.25, 0.5 or 0.75 l/ha). The average day temperature was 23° C., precipitation was 300 mm, and relative humidity 87%. Pregerminated seed was broadcast. Weed control was done using a mix of 6 liters STAM® LV10 and 0.5 liter agroxone (MCPA, ICI) per hectare. Urea fertilizer was applied at 200 kg/ha. Application of ETHREL® ethephon was done using a knapsack sprayer.

Results

Table V presents data of the experiments:

TABLE V

| ETHREL® (g ai/ha) | Number of Panicles/m² | 100 Grain weight in grams | Yield kg/ha |
| --- | --- | --- | --- |
| 120 | 485 | 25.9 | 3,272 |
| 240 | 550 | 28.1 | 4,560 |
| 360 | 535 | 27.5 | 5,288 |
| Control | 465 | 25.4 | 3,344 |

Periodic observations indicated that ETHREL® ethephon produced a significant hardening or stiffening of the stem tissue. The number of panicles/m², grains per panicle, and grain weight was higher for crops treated with ethephon at rates of 240 and 360 g a.i./ha for control crops. Furthermore, a significant increase in yield was obtained at rates of 240 and 360 grams per hectare.

EXAMPLE 4

The experiment was carried out in Nobol, Ecuador, using 77 day-old transplants of rice cultivar INIAP 415. Each treatment was conducted on 10 hectare plots.

Transplanting was done on September 20, 1984. Ten weeks after transplanting, plots were sprayed with ETHREL® ethephon at rates of 240 and 360 g/ha using a knapsack spray system. At this time, flower primordia length is 5 mm.

Three applications of nitrogen were made (112 kg urea, 112 kg urea and 21 kg ammonia sulphate). Herbicides e.g. propanil, insecticides and miticides were used during the test to control weeds, armyworms, and mites.

Results

ETHREL® 480 applied at rates of 240 and 360 g/ha, produced significantly higher yields than the control. Results are shown in Table VI.

TABLE VI

| Treatments | (g ai/ha) | Grain Yield/ha Kg | Increase over Control (%) |
| --- | --- | --- | --- |
| ETHREL® 480 | 240 | 5,485 | 14.7 |
| ETHREL® 480 | 360 | 7,340 | 53.49 |
| Control | — | 4,782 | — |

EXAMPLE 5

Rice crop was planted in Ecuador on Dec. 20, 1984, and harvested June 6, 1985. ETHREL® 480 ethephon treatment was done 65-76 days after planting, at the stage when the flower primordia was just formed (about 2-3 mm in length). Application rates were either 240 or 360 g/ha (0.25 or 0.75 l/ha). Application of ETHREL® ethephon was done using backpack sprayer.

Results

Results are shown in Table VII.

TABLE VII

| ETHREL® (g ai/ha) | Plant Height Before Application | Plant Height At Harvest | Number of Panicles/m² |
| --- | --- | --- | --- |
| 240 | 66 cm. | 92 cm. | 474 |
| 360 | 64 | 88 | 414 |
| Control | 66 | 80 | 330 |

| ETHREL® (g ai/ha) | Panicle Length | Number Grains Per Panicle | 1000 Grain Weight | Yield |
| --- | --- | --- | --- | --- |
| 240 | 25 cm. | 169 | 30.6 g | 8,381 kg/ha |
| 360 | 24 | 136 | 29.7 | 7,746 |
| Control | 22 | 137 | 30.0 | 7,058 |

Plant height at harvest, number of panicles, and yield were significantly greater when ETHREL® was applied.

EXAMPLE 6

ETHREL® ethephon was applied to rice crop (rice variety CR-1113) in Costa Rica. About 16 hectares were treated from the air with a dosage of ETHREL®ethephon 480 of 500 ml/ha at the time the flower primordia was first formed. ETHREL® ethephon was tankmixed with fungicides and foliar fertilizers. A control of approximately 16 hectares was maintained. Weed control was done with arrosols and hormonals.

The crop was affected by draught which reduced the number of tillers per Plant. Harvesting was done on Nov. 28, 1984.

Results

Table VIII shows experimental results.

TABLE VIII

| ETHREL® 480 | Number of Panicles/Plant | Number Grains Per Panicle |
| --- | --- | --- |
| 0.5 (l/ha) | 3.4 | 9.2 |
| Control | 2.4 | 66.25 |

The number of panicles per plant and number of grains per panicle were significantly greater with application ETHREL® 480.

What is claimed is:

1. A method of increasing the yield of rice plants, comprising applying ethephon to said plants, when said plants have progressed to a growth stage between about the end of effective tillering and about the initiation of panicle primordia, at rates from about 100 to about 500 grams per hectare.

2. A method as defined in claim 1, wherein said rates are from about 200 to about 400 grams per hectare.

3. A method as defined in claim 1, wherein said rates are from about 240 to about 360 grams per hectare.

4. A method as defined in claim 1, wherein application of ethephon is done by hand-held $CO_2$ charged sprayer.

5. A method as defined in claim 1, wherein application of ethephon is done by backpack sprayer.

6. A method as defined in claim 1, wherein application of ethephon is done by tractor-drawn sprayer.

7. A method as defined in claim 1, wherein application of ethephon is done by aerial sprayer.

8. A method as defined in claim 1, wherein the plants are at a growth stage about 7–10 days before initiation of panicle primordia.

9. A method as defined in claim 1, wherein the plants are at a growth stage about 7–10 days before maximum tillering.

10. A method as defined in claim 1, wherein the plants are at a growth stage of initiation of panicle primordia.

* * * * *